(12) United States Patent
Teumer et al.

(10) Patent No.: US 7,785,876 B2
(45) Date of Patent: Aug. 31, 2010

(54) CULTIVATION OF HAIR INDUCTIVE CELLS

(75) Inventors: Jeffrey Keller Teumer, Brookline, MA (US); Erica Philips, Lowell, MA (US); Richard Gregory Wolowacz, Derbyshire (GB); Jizeng Qiao, Lexington, MA (US)

(73) Assignee: Aderans Research Institute, Inc., Marietta, GA (US)

( * ) Notice: Subject to any disclaimer, the term of this patent is extended or adjusted under 35 U.S.C. 154(b) by 0 days.

(21) Appl. No.: 10/534,428

(22) PCT Filed: Nov. 14, 2003

(86) PCT No.: PCT/GB03/04949

§ 371 (c)(1), (2), (4) Date: May 10, 2005

(87) PCT Pub. No.: WO2004/044188

PCT Pub. Date: May 27, 2004

(65) Prior Publication Data

US 2005/0272150 A1 Dec. 8, 2005

Related U.S. Application Data

(60) Provisional application No. 60/426,111, filed on Nov. 14, 2002.

(51) Int. Cl.
*C12N 5/00* (2006.01)
(52) U.S. Cl. .......................... 435/325; 435/4; 435/371; 424/93.7
(58) Field of Classification Search ................. 435/383, 435/325
See application file for complete search history.

(56) References Cited

U.S. PATENT DOCUMENTS

| | | | |
|---|---|---|---|
| 4,919,664 A | 4/1990 | Oliver et al. | |
| 5,002,881 A * | 3/1991 | Van Nispen et al. | 435/139 |
| 5,540,657 A | 7/1996 | Kurjan et al. | |
| 5,554,153 A | 9/1996 | Costello et al. | |
| 5,571,083 A | 11/1996 | Lemelson | |
| 5,611,811 A | 3/1997 | Goldberg | |
| 5,620,421 A | 4/1997 | Schmitz | |
| 5,685,860 A | 11/1997 | Chang et al. | |
| 5,851,831 A | 12/1998 | Inamatsu et al. | |
| 5,899,916 A | 5/1999 | Casparian | |
| 5,908,416 A | 6/1999 | Costello et al. | |
| 6,224,567 B1 | 5/2001 | Roser | |
| 6,383,220 B1 | 5/2002 | Van Blitterswijk et al. | |
| 6,399,057 B1 | 6/2002 | Gho | |
| 6,497,875 B1 | 12/2002 | Sorrell et al. | |
| 6,790,455 B2 | 9/2004 | Chu et al. | |
| 2001/0027293 A1 | 10/2001 | Joshi | |
| 2005/0089512 A1 | 4/2005 | Schlotmann et al. | |
| 2005/0272150 A1 | 12/2005 | Teumer et al. | |

FOREIGN PATENT DOCUMENTS

| | | | |
|---|---|---|---|
| EP | 0236014 | | 9/1987 |
| WO | WO 98/47471 | | 10/1998 |
| WO | WO 99/01034 | * | 1/1999 |
| WO | WO 00/09184 | | 2/2000 |
| WO | WO 00/49138 | | 8/2000 |
| WO | WO 00/69449 | * | 11/2000 |
| WO | WO 01/11011 | | 2/2001 |
| WO | WO 01/12252 | | 2/2001 |
| WO | WO 01/32129 | | 5/2001 |
| WO | WO 01/32840 | | 5/2001 |
| WO | WO 01/58413 | | 8/2001 |
| WO | WO 01/74164 | | 10/2001 |
| WO | WO 02/060396 | | 8/2002 |

OTHER PUBLICATIONS

Keller et al, Frontiers in Bioscience, vol. 1,1996, p. 59-71 (1-21).*
Hibberts et al, Journal of Endocrinology, vol. 156, 1998, p. 59-65.*
Zhu et al, Cancer Research, 2004 p. 7918-7926.*
Jahoda et al., "Induction of Hair Growth by Implantation of Cultured Dermal Papilla Cells," *Nature* 311:560-562 (1984).
Kishimoto et al., "Wnt Signaling Maintains the Hair-Inducing Activitiy of the Dermal Papilla," *Genes Dev.* 14:1181-1185 (2000).
Inamatsu et al., "Establishment of Rat Dermal Papilla Cell Lines that Sustain the Potency to Induce Hair Follicles from Afollicular Skin," *J. Invest. Dermatol.* 111:767-775 (1998).
Alltech Associates, Inc., "Hamilton Manual Syringe Dispensers and Pipettes," Data Sheet D84250, 1998.
Gravesen et al., "Microfluidics—A Review," *J. Micromech. Microeng.* 3:168-182, 1993.
Matsuzaki et al., "Hair Induction by Dermal Papilla Cells Cultured with Conditioned Medium of Keratinocytes," *Elsevier Science B.V.* 447-451, 1996.
Toma et al., "Isolation of Multipotent Adult Stem Cells from the Dermis of Mammalian Skin," *Nature Cell Biology* 3: 778-784, 2001.
International Search Report for International Application No. PCT/GB 03/00587, mailed on Jul. 17, 2003.
Matsuzaki et al. "Hair Induction by Dermal Papilla Cells Cultured with Conditioned Medium of Keratinocytes." In *Hair Research for the Next Millenium* (D. van Neste, V. A. Randall, Eds.) Elsevier, Amsterdam, pp. 447-451, 1996.

* cited by examiner

*Primary Examiner*—Jon P Weber
*Assistant Examiner*—Tiffany M Gough
(74) *Attorney, Agent, or Firm*—Pabst Patent Group LLP

(57) ABSTRACT

The present invention relates to culturing cells which may be used in hair induction. In one aspect of the invention there is provided a method for cultivation of hair inductive cells, comprising the step of culturing the hair inductive cells in a culture medium comprising a medium conditioned by conditioning cells, in which the conditioning cells are derived from non-epidermal tissue.

20 Claims, 4 Drawing Sheets

CULTIVATION OF HAIR INDUCTIVE CELLS

CROSS-REFERENCE TO RELATED APPLICATIONS

This application is a U.S. National Stage Application under 35 U.S.C. §371 of International Application PCT/GB2003/004949, filed Nov. 14, 2003, and claims benefit from U.S. Provisional Application No. 60/426,111, filed Nov. 14, 2002.

The present invention relates to culturing cells for use in hair induction. In particular, the invention relates to a method for cultivating hair inductive cells (for example, dermal papilla and/or dermal sheath cells), cells cultivated according to method, and use of these cultivated cells.

Hair loss affects millions of people, including over 40% of men over the age of 30 and a significant number of women. Many people seek remedy in a variety of pharmaceuticals and other treatments including for example locally-delivered Minoxidil™ (Pharmacia) and orally-delivered Propecia™ (Merck). One solution to hair loss is hair follicle transplantation, a procedure in which hairs from a non-balding region of the scalp are transplanted to bald areas. The follicles from the non-balding region retain their low susceptibility to androgens even in their new location. However, this procedure is limited by the relatively small number of hair follicles that can be harvested from the non-bald region and "donated" to the hairless region. A complete pattern of hair with equivalent density of follicles to that typical for example of teenagers cannot be readily obtained using hair follicle transplantation.

Dermal papilla cells (DP cells) can be removed from hair follicles (e.g. derived from non-balding sites) and directly transplanted to another place in the skin where they will instruct the skin to form new hair follicles (Oliver, R. F., 1967, J. Embryol. Exp. Morphol. 18(1): 43-51). This procedure could be developed into an alternative therapy for hair restoration. However, an impediment to the development of this alternative therapy has been that it is subject to the same limitation on the availability of donor follicles.

DP cells can expand in number when placed into culture using conventional conditions but under these conventional conditions they rapidly lose their ability to induce new hair formation (Jahoda, C. & Oliver, R. F., 1981, Br. J. Dermatol. 105(6): 623-7; Messenger, A. G., 1984, Br. J. Dermatol. 110 (6): 685-9). Something present in vivo that preserves DP cell hair inductive ability is therefore lacking in conventional cell culture medium. A hair transplantation process using DP cell transplantation is not commercially viable without a culture method which allows expansion of cell number without loss of inductive ability.

Recently, two methods have been described that are able to support expansion of cell number while also maintaining the hair inductive potential of DP cells. In a first method, conditioned medium (CM) collected from mammalian epidermal cells (keratinocytes), or co-culture with keratinocytes, were shown to support both expansion of DP cell number and maintenance of the hair inductive phenotype over several culture passages. This first method is described in U.S. Pat. No. 5,851,831 and in J. Invest. Dermatol. 111: 767-75 (1998).

A second method describes the culture of dermal papilla cells in the presence of an increased level of wnt protein or an agent that mimics the effects of wnt-promoted signal transduction (see International Patent Application No. PCT/US01/10164 published as WO 01/74164 and Kishimoto et al., 2002, Genes & Development 14: 1181-85). In this second method, a wnt protein or a functional fragment or analogue thereof is added to the culture medium as a purified product, or by expressing a recombinant protein in producer cells and providing the wit protein in medium conditioned by the growth of wnt producer cells, or by co-culture with producer cells.

Some problems with the known methods are of a practical nature relating to regulatory issues, manufacturing costs, and technical problems. For the first method, normally a manufacturer will cryopreserve a large number of cells to provide a bank of cells with identical properties that can be used in manufacture. Cells from this bank will need to undergo stringent tests for safety, including tests that screen for infectious agents that could potentially cause disease in human recipients. Eventually, the cell bank will be depleted and will need to be replenished, and the new bank will require new testing. In the case of a cell strain derived from primary tissue, such as sole skin keratinocytes that have a limited life span in culture, the size of the cell bank will be limited by the ability of the cells to grow in culture, so the costs associated with the use of such a tissue source will be greater than they would be if the original cell were available in unlimited supply. In addition, there can be variations between the donors of the original cell strains that may result in irreproducible manufacturing conditions. Use of an alternative cell source, such as those described herein, provides an unlimited source of cells with uniform properties that only have to be tested once.

In the second method described above, where CM from a recombinant wnt producing cell is used to promote DP cell growth, similar testing would be minimally required. However, because the cells are producing recombinant protein, additional safety tests are required. The stability of wnt gene expression in these producer cells is also a potential problem, and it may be necessary to re-derive or sub-clone the cells in the event wnt gene expression is lost or reduced over time in culture.

The present invention address problems associated with the prior art by allowing culture of hair inductive cells using an alternative cell source with uniform properties.

According to a first aspect of the present invention there is provided a method for cultivation of hair inductive cells, for example allowing for hair inductive potential of the hair inductive cells to be maintained, comprising the step of culturing the hair inductive cells in a culture medium comprising a medium conditioned by conditioning cells, in which the conditioning cells are derived from non-epidermal tissue.

The ability of a medium conditioned by conditioning cells derived from non-epidermal tissue to maintain hair inductive phenotype of hair inductive cells was highly unexpected. In contrast to U.S. Pat. No. 5,851,831, where keratinocytes that would interact in vivo with epidermal cells to form hair cells, the non-epidermal tissue-derived cells used in the present invention are not necessarily associated in vivo with hair inductive cells. Thus the present invention shows that various terminally differentiated cells or committed progenitor cells which are not epidermal may be used in place of keratinocytes to condition medium to retain the hair inductive potential of hair inductive cells during the culture expansion phase important in any process to produce large number of hairs, for example from a small biopsy containing relatively few follicles.

In one aspect, the tissue from which conditioning cells are derived is non-ectodermal.

The tissue may be of mesodermal origin. An example of conditioning cells of mesodermal origin within the scope of the invention are prostate epithelial cells, which are shown in the experimental section below to be particularly effective at maintaining hair inductive capability of hair inductive cells in culture. In another embodiment, the conditioning cells are human dermal fibroblasts. Other examples of mesodermal origin cells are renal epithelial cells, endothelial cells and immune system cells. In one aspect of the invention, the cells of mesodermal origin do not include skeletal muscle myoblast cells. It is surprising that cells of mesodermal origin which are not normally found in close proximity to hair inductive cells such as DP cells, unlike the keratinocytes used in U.S. Pat. No. 5,851,831 can nevertheless provide similar cues to the hair inductive cells to retain their inductive potential.

In another embodiment the invention uses conditioned medium derived from cells of endodermal origin. Examples of endodermal origin cells are hepatocytes and bladder epithelium. The ability to use endodermal-derived cells is, as for mesodermal cells, surprising as it represents a cell type from a different embryological layer than epidermal cells.

In one aspect of the invention, the hair inductive potential of the hair inductive cells is maintained.

The method may be used for long-term culture of hair inductive cells. Long term culture may be defined by either passage number or more properly by population doublings. Primary fibroblasts, keratinocytes, and satellite cells can sometimes be expanded for up to 120 population doublings from young donors. For example, when fibroblasts are split 1 in 3 during passage they can reach up to passage 40 before becoming senescent. However, if the plating density used was lower then they would undergo more population doublings between each passage. In absolute terms this would be a long-term culture. Sufficient hair inductive cells (for example, DP cells) for transplantation of a full pattern of hair may be obtained from less than 30 follicles by passage up to p3 (passage 3) using optimal plating density for the cells. The method may therefore allow for long-term culture of hair inductive cells while keeping the original capability (i.e. hair inductive potential) of the cells intact.

The culture medium may consist essentially of the conditioned medium. The culture medium may comprise conditioning cells derived from the non-epidermal tissue. The conditioned medium may thus be produced "in situ" by the conditioning cells derived from non-epidermal tissue as the conditioning cells grow in the presence of the hair inductive cells.

The hair inductive cells may be dermal papilla (DP) cells and/or dermal sheath (DS) cells.

The conditioned medium may be obtained using a cell line (for example, an established cell line). Suitable cell lines may be more readily available or more convenient to culture compared with existing methods for proliferating hair inductive cells. Thus, in contrast to the culture medium described in U.S. Pat. No. 5,851,831 and WO 01/74164, the culture medium of the present invention may be prepared from a stable cell line that is available in a virtually unlimited supply. Alternatively, the culture medium may be prepared from a non-epidermal tissue-derived cell strain that is more readily available or more convenient to culture.

The cell line may be derived from a donor that has been screened and tested for risk factors associated with transplantation.

The culture medium may be free of recombinant genes and/or recombinant products thereof. The culture medium may be free of viral vectors. Recombinant genes and their products and viral vectors may raise safety concerns that are avoidable using the present method.

The conditioned medium may be frozen prior to use.

When sub-culturing hair inductive cells, the culture medium may be completely changed or the cells may be split fed by changing only part of the medium for example by adding fresh conditioned medium.

The conditioned medium may generated from cells grown in serum-free medium. The potential problem of transmission of infectious agents potentially present in serum has led to the use of closed herds for generating serum used in the manufacture of cellular products. These infectious agents include bovine spongiform encephalopathies (BSE). There may be significant regulatory advantages for a process a totally free of the use of serum.

In one embodiment, the conditioning cells are cultured in an appropriate defined medium. Defined media will be known to those skilled in the art, suitable for the propagation and culture of each cell type which may be used for the generation of conditioned medium described in this invention.

The conditioned medium may have a serum-free component with a total protein content above 10 µg/ml, for example above 100 µg/ml or above 1 mg/ml. In serum-containing medium, serum will normally be the major protein component.

The conditioned medium may concentrated (for example, by ultrafiltration) prior to use. This will allow for concentration of factors necessary to maintain hair inductive phenotype.

In another aspect of the invention, the method further comprises the step of subculturing the hair inductive cells in the culture medium for three or more passages, for example seven or more passages. For example, the hair inductive cells may undergo about 30 population doublings before use.

The method may further comprise the step of harvesting or isolating cultured or subcultured hair inductive cells.

The hair inductive cells may be allogeneic to the non-epidermal tissue. Alternatively, the hair inductive cells may be autologous to the non-epidermal tissue.

Features described in relation to the first aspect of the present invention relate also to other aspects of the invention described herein.

According a further aspect of the invention there is provided a method of long term cultivation of dermal papilla (DP) cells and/or dermal sheath (DS) cells of a mammalian species, the method comprising the steps of culturing and sub-culturing the DP and/or DS cells in a cell culture medium which consists essentially of, or is supplemented with, a medium conditioned by one or more mammalian cells derived from a non-epidermal tissue (for example, non-ectodermal tissue such as mesodermal tissue and/or endodermal tissue), thereby proliferating the DP and/or DS cells while preserving their hair inductive potential.

In another aspect, there is provided a method of providing and maintaining dermal papilla (DP) and/or dermal sheath (DS) cells for transplantation, the method comprising the steps of obtaining a DP and/or DS cell from a subject and culturing the DP and/or DS cell as described above.

According to further aspect of the present invention there is provided a method for cultivation of hair inductive cells, comprising the step of culturing the hair inductive cells in a co-culture system, whereby the hair inductive cells are provided necessary factors for the maintenance of hair inductive phenotype by feeder cells, preferably non-epidermal feeder cells. These feeder cells are preferably in the same culture vessel. In such a co-culture system, the feeder cells, which are cells that provide the factors to the hair inductive cells, provide culture support either through intermingling with the hair inductive cells or through a membranous barrier where the cells are kept separate but share the same culture medium.

Where the two cell types are cultured in an intermingled arrangement, the feeder cells may be mitotically inactivated so they cannot divide and will therefore not significantly contaminate the hair inductive cells for transplantation.

Mitotic inactivation may be accomplished by drug treatment or by irradiation, techniques known to those skilled in the art. Where a membranous barrier is used, the feeder cells may be separated from the hair inductive cells by a permeable membrane that allows the exchange of medium but does not allow cell types to contact each other. This prevents contamination of hair inductive cells by the feeder cells. Examples of co-culture system that use a membrane barrier are transwell plates and Boyden chambers and are known to those skilled in the art.

The invention also provides cultured hair inductive cells, for example DP cells and/or DS cells, obtainable using the methods described herein.

The invention further provides the use of the cultured hair inductive cells, for example DP cells and/or DS cells, obtainable using the methods provided herein for the treatment (for example, cosmetic treatment) of male pattern baldness.

Also provided is the use of the cultured hair inductive cells, for example DP cells and/or DS cells, obtainable using the methods described herein in the production of in vitro skin equivalents.

In a further aspect of the invention, there is provided a composition comprising hair inductive cells and a culture medium comprising a medium conditioned by conditioning cells derived from non-epidermal tissue (for example, non-ectodermal tissue such as mesodermal tissue and/or endodermal tissue).

The invention also provides a culture medium for cultivation of hair inductive cells, in which the culture medium comprises a medium conditioned by non-epidermal cells (for example, mesoderm-derived cells such as prostate epithelial cells, and/or endoderm-derived cells) and is capable of maintaining hair inductive potential of the hair inductive cells.

Conditioned medium, i.e. medium conditioned by cells derived from non-epidermal tissue, may be defined as a spent medium obtained by the growth of living cells in culture medium. Conditioned medium contains numerous secreted factors expressed and secreted by the cultured living cells into the culture medium. These secreted factors would include numerous molecules and macromolecules (proteins, glycoproteins such as growth factors, proteases, soluble receptors, hormones, etc.) as well as waste products produced by the conditioning cells. Different lineages of cells express different phenotypes and will therefore secrete different sets of factors, and/or factors at different concentrations, into the culture medium. Therefore, a conditioned medium from a fibroblast culture for example will contain different molecules in different concentrations to a conditioned medium from a keratinocyte culture.

Typically living cells may be grown in a monolayer culture in a variety of containers including on the surface of standard tissue culture flasks (e.g. T175 or T75), roller bottles or on micro-carrier beads. Conditioned medium may include one or more known basal media (e.g. DMEM, Chang's, Hams F12, etc). Conditioned medium may also be derived from three dimensional cell cultures or culture of a tissue or organ. Conditioned medium may be derived from culture in both serum free or serum supplemented media. Optimisation of the length of time of culture require for cells to secrete factors at sufficient concentration and/or the volume of culture medium to be used for a given number of cells may be developed empirically by those skilled in the art. In general terms, the higher the number of cells for a given volume, and the longer the cells are cultured to produce a conditioned medium, the higher the concentration of "secreted factors" typical of a cell lineage.

Conditioned medium may be tested for activity according to the invention as described in the experimental section below. It may be desirable to adopt a quality assurance approach in closely defining all procedures to ensure manufacture of a conditioned medium is consistent. For example, cell plating density, feeding regimes, volume of culture medium, basal medium and/or supplements could be accurately defined and applied.

In one embodiment of the invention, the hair inductive cell culture obtained, i.e. the "product" derived, is autologous. Hair inductive cells such as DP and/or DS cells are taken from one biopsy. Specific non-epidermal cells are derived from another biopsy and cultured so as to provide the conditioned medium. This conditioned medium is added to the DP and/or DS cells to allow them to retain the inductive potential. Typically the DP and/or DS cells can be derived from a skin biopsy of 1-2 $cm^2$ containing on average 400 follicles and is expanded (for example, to passage 3) to obtain sufficient cells for DP and/or DS cell transplantation by a hair surgeon or otherwise.

In another embodiment of the invention, only the DP and/or DS cellular component is autologous. The DP and/or DS cells are obtained as above from a biopsy. However the non-epidermal cells from which the conditioned medium is derived are obtained from a separate source (preferably an allogeneic or xenogeneic source). This source would preferably be from a validated cell bank which has been screened for adventitious agents. Because these cells are stored as master cell banks it may be possible to manufacture large amounts of conditioned medium using known tissue culture methods. In this case, the conditioned medium could then be concentrated via standard protein methods e.g. ultrafiltration and stored as a concentrated stock, to be added to the DP and/or DS cells as a supplement as appropriate. This approach has certain advantages in that if a large batch of conditioned medium is prepared, a small sample can be tested for its ability to allow DP and/or DS cells to retain their inductive potential in a hair induction assay. Because hair induction assays are time consuming, there may be further advantages in confidence in use of the expanded DP and/or DS cells to using an additive from batch with a quality control (QC)-tested activity. This contrasts with the method of U.S. Pat. No. 5,851,831 in which keratinocyte conditioned medium may be used without knowing from a QC test whether the activity causing the retention of hair inductive capability of DP and/or DS cells has been retained.

In a further embodiment of the invention, the DP and/or DS cells to be expanded may be derived from an allogeneic source. This may be used in conjunction with conditioned medium derived from allogeneic source as described above. The DP and/or DS cells would by preference also be from a cell source screened for the presence of adventitious agents and from a source approved by appropriate regulatory agencies.

The invention therefore addresses previous block to the development of a reproducible, cost-effective process for commercialisation of hair inductive cell (for example DP and/or DS cell) transplantation.

Specific embodiments of the invention will be described below with reference to the accompanying figures, of which:

EXPERIMENTAL

The experiments described below demonstrate cultivation of DP cells in different media to show that growth in conditioned medium (CM) of the present invention results in maintenance of hair inductive capability and morphology associated with hair inductive capability.

Materials and Methods

Preparation of Conditioned Medium (CM)

When cells grown for test CM reached a near-confluent stage, fresh medium was applied. After 5 days, the medium was removed and filtered through a 0.22 μm filter to remove cells and debris. The CM was combined with fresh medium at a 1:1 (volume: volume) ratio and used to feed cultured dermal papilla cells. CM was generated from human keratinocytes grown under standard conditions.

Cell Lines

The following cell types of ectodermal origin were tested: 2 human breast tumor cell lines; MCF-7 (American Type Culture Collection; ATCC) and MDA-MB-231 (ATCC); and embryonal carcinoma cell line, N-tera-2 (P. Andrews, Sheffield, UK), human mammary epithelial cells (Cascade Biologics, Oregon, USA), and human melanocytes (Cambrex, New Jersey, USA). The following cell types of mesodermal origin were tested: human dermal fibroblasts (HDF, which were isolated from freshly excised human tissue and grown under standard conditions), skeletal muscle myoblasts (Cambrex), prostate epithelial cells (Cambrex). Other cell types available for testing are: renal epithelial cells, endothelial cells, and immune system cells (of mesodermal origin); and hepatocytes and bladder epithelium (of endodermal origin). Unless otherwise stated, cell types were cultured under conditions recommended by the suppliers.

Human DP Cell Culture

Human DP were placed into culture after microdissection of DP from hair follicles. After 5 days in standard medium, media were replaced with test CM. Culture media were replaced every 2-3 days and cultures were passaged when confluent. Cultures were maintained in this manner for several passages. Cells shown in FIGS. 2 and 3 were photographed at passage 3.

Assay for Hair Induction

The skin reconstitution assay (Lichti, et al., 1993, J Invest. Dermatol. 101: 124S-129S; and Weinberg et al., 1993, J Invest. Dermatol. 100: 229-236) was used to test for hair induction by the cultured hair inductive (for example, DP) cells. Circular, full-thickness wounds were made on the backs of athymic mice and a graft chamber was placed into the wounds. Rodent keratinocytes mixed with either cultured dermal papilla cells or dermal fibroblasts (as a negative control) were injected into the graft chambers. After one week the chambers were removed and the wounds were bandaged. The engrafted cells formed full-thickness skin and, if hair-inductive dermal papilla cells are present, new hair follicles also formed. The new hairs induced by the DP cells appeared within 4 weeks of grafting.

RESULTS AND DISCUSSION

Figure 1:
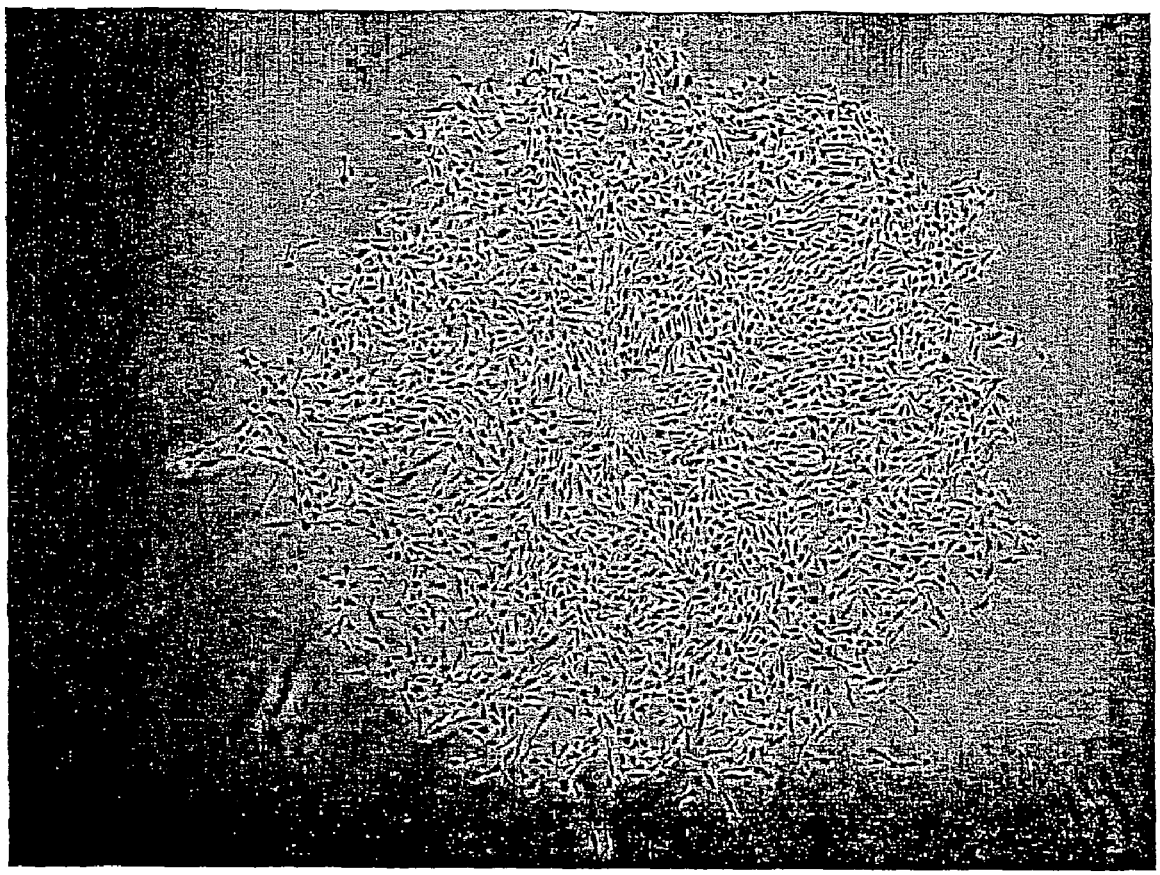
FIG. 1 is a photograph showing dermal papilla cells soon after isolation.

Dermal papilla cells have a characteristic morphology when first isolated. The cells are small and round or polygonal and grow in loose clusters (FIG. 1). Within some early cultures, there are also large, flat cells that do not divide. Over time in culture in standard medium, the proportion of large, flat cells increases. These cells have a reduced ability to induce hair follicle formation. Thus, morphology observed under ideal culture conditions can be seen as a first indication of hair induction ability.

Figure 2:
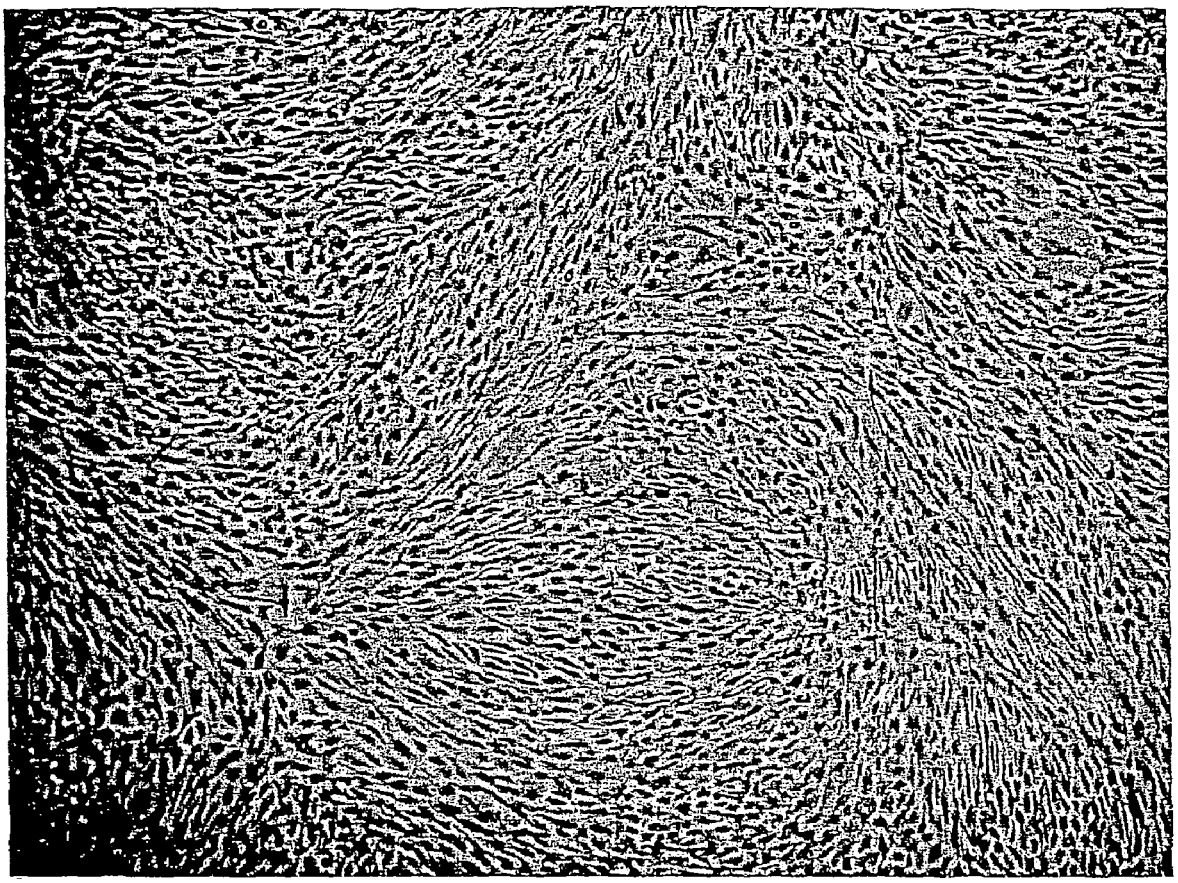
FIG. 2 is a photograph showing dermal papilla cells grown in keratinocyte CM.

When DP cells are cultured using keratinocyte-derived CM (as described in U.S. Pat. No. 5,851,831) the characteristic morphology is maintained over numerous passages. FIG. 2 shows a culture of DP cells grown to passage 7 in keratinocyte CM. In this medium, the cells maintain their morphology as well as their ability to induce hair formation.

Figure 3:
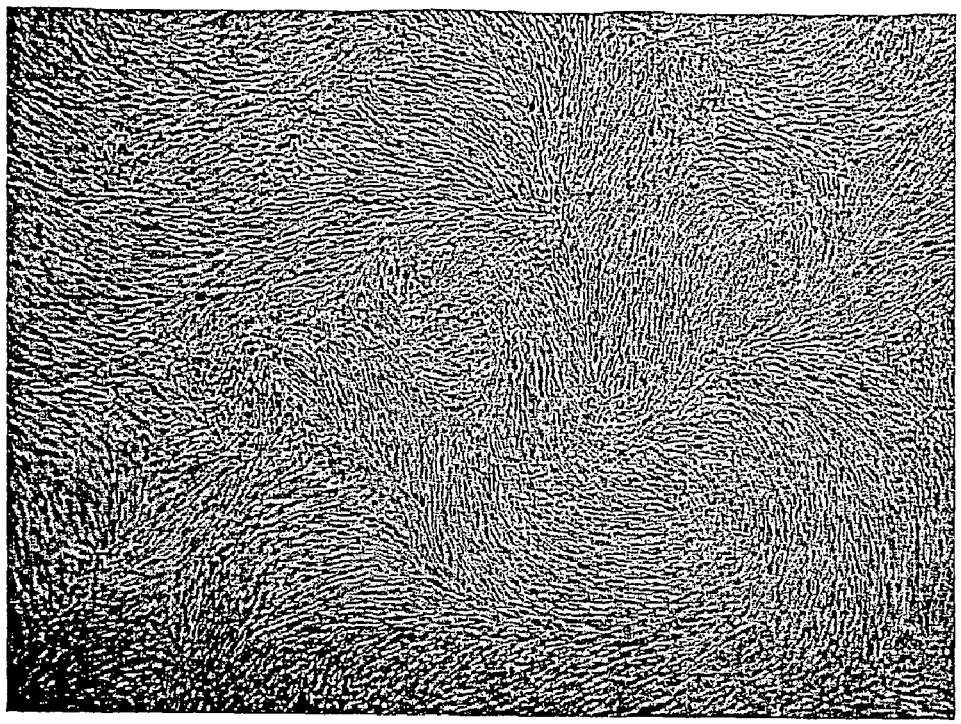
FIG. 3 is a photograph showing dermal papilla cells grown in CM collected from human prostate epithelia cells.

DP grown in CM collected from human prostate epithelia cells are shown in FIG. 3. These cells are close in morphology to the keratinocyte CM grown cells, suggesting that human prostate epithelia-conditioned medium is capable of maintaining the ability of DP cells to induce hair formation.

In further experiments, human DP cells or negative control cells were grown in the presence of various conditioned or control media as described above. After 21 days in culture, cells were tested for hair induction in the skin reconstitution assay. Where hair induction takes places, new hairs can be seen growing from grafts usually within 4 weeks of grafting.

Figure 4:
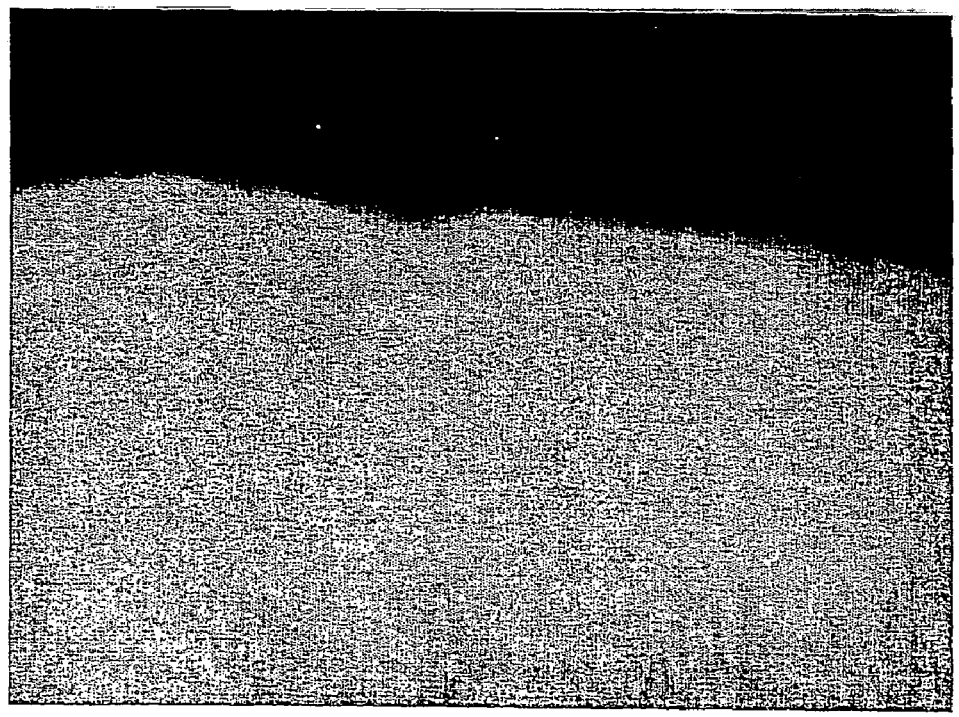
FIG. 4 is a photograph showing a graft generated using the skin reconstitution assay in which the engrafted dermal cells were human dermal fibroblasts, which are not expected to induce hair growth.
Figure 5:
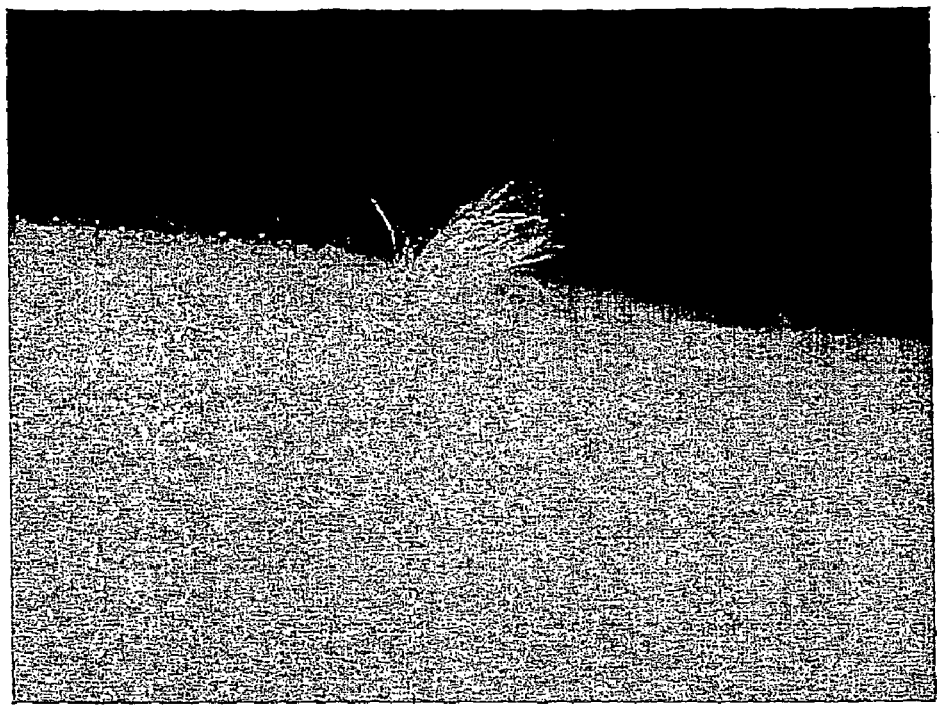
FIG. 5 is a photograph showing a graft generated using the skin reconstitution assay in which the engrafted dermal papilla cells were grown in keratinocyte CM.
Figure 6:
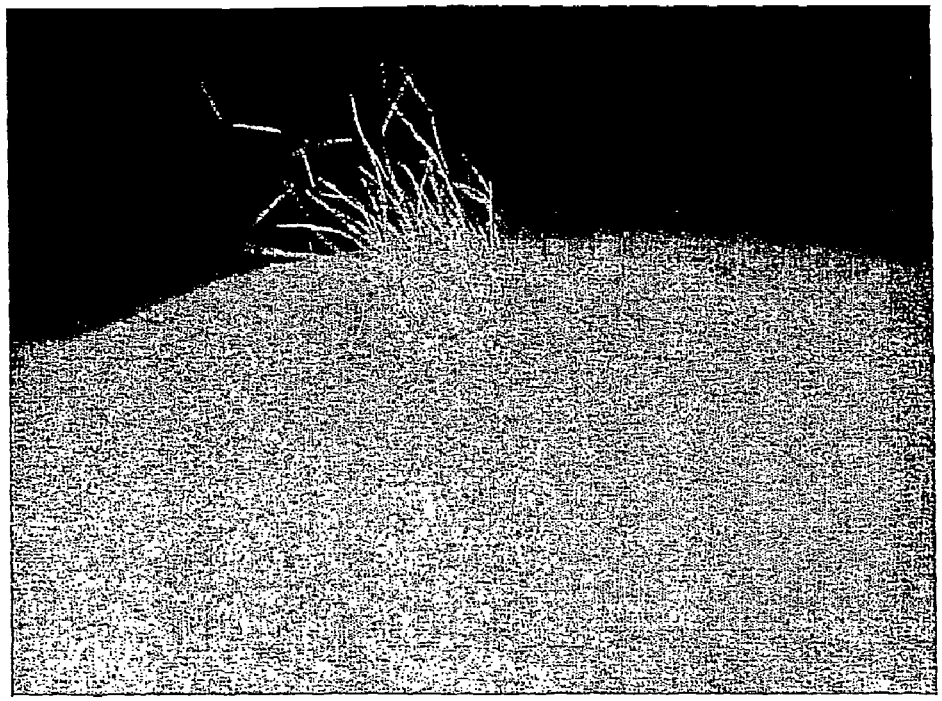
FIG. 6 is a photograph showing a graft generated using the skin reconstitution assay in which the engrafted dermal papilla cells were grown in prostate epithelial cell CM.

FIGS. 4 to 6 are photographs showing skin reconstitution assay results. FIG. 4 shows results from a negative control experiment in which human dermal fibroblasts grown in standard medium were implanted and failed to induce hair formation. FIG. 5 shows a positive control experiment in which DP cells grown in keratinocyte-derived CM (as described in U.S. Pat. No. 5,851,831) were implanted and induced hair formation. As can be seen in FIG. 6, DP cells grown in prostate epithelial cell-derived CM induced hair formation in quantities similar to the amount of hair induced by DP cells grown in keratinocyte CM (FIG. 5). Thus, like keratinocytes, prostate epithelial cells condition media in such a way as to make the media capable of maintaining the hair inductive potential of DP cells.

Table 1 lists results from the skin reconstitution assay. Of the cultures tested, DP cells grown in prostate epithelial cell CM gave the strongest hair induction. DP grown in human dermal fibroblast (HDF) CM showed modest hair induction. CM from skeletal muscle myoblasts did not appear to support hair induction. DP cultures grown in melanocyte CM or N-Tera-2 CM failed to induce hair growth. Likewise, DP cells grown in CM from the other examples of ectoderm-derived cell types, i.e. the mammary epithelia (including two mammary tumor cell lines), failed to induce hair growth.

TABLE 1

| CM Cell Source | # Grafts with Hair/ # Grafts | Germline Origin |
| --- | --- | --- |
| Melanocytes | 0/3 | Ectoderm |
| MCF-7 (Mammary Carcinoma) | 0/2 | Ectoderm |
| MDA-MB-231 (Mammary Carcinoma) | 0/3 | Ectoderm |
| Mammary Epithelium | 0/3 | Ectoderm |
| N-tera-2 | 0/4 | Ectoderm |

TABLE 1-continued

| CM Cell Source | # Grafts with Hair/ # Grafts | Germline Origin |
|---|---|---|
| Human Dermal Fibroblast | 1/3 | Mesoderm |
| Skeletal Muscle Myoblast | 0/4 | Mesoderm |
| Prostate Epithelium | 3/3 | Mesoderm |

The interaction between keratinocytes, an epithelial cell type, and DP cells, a mesenchymal cell type, is similar to other epithelial-mesenchymal interactions in the body. Epithelial-mesenchymal interactions are fundamental processes that occur during embryogenesis and they contribute to the formation of many organs and other structures in the body. These interactions are mediated by signaling molecules produced by one cell type that instruct the other cell type to respond in a characteristic manner. The present invention demonstrates that, surprisingly, keratinocytes can be replaced by another cell type that produces the same or similar signaling molecule in order to obtain the response in a mesenchymal cell. These other cell types as described herein are thus able to maintain hair inductive cells in a hair inductive state in culture.

The invention claimed is:

1. A method for cultivation of hair inductive cells, comprising the step of culturing the hair inductive cells in a culture medium comprising prostate epithelial cells and medium conditioned by said prostate epithelial cells.

2. The method of claim 1, in which the hair inductive potential of the hair inductive cells is maintained.

3. The method of claim 1, in which the culture medium consists essentially of the conditioned medium.

4. The method of claim 1, in which the hair inductive cells are dermal papilla (DP) cells and/or dermal sheath (DS) cells.

5. The method of claim 1, in which the conditioned medium is obtained using a cell line.

6. The method of claim 5, in which the cell line is derived from a donor that has been screened and tested for risk factors associated with transplantation.

7. The method of claim 5, wherein said cell line is an established cell line.

8. The method of claim 1, in which the culture medium is free of recombinant genes and/or recombinant products thereof.

9. The method of claim 1, in which the culture medium is free of viral vectors.

10. The method of claim 1, in which the conditioned medium is frozen prior to use.

11. The method of claim 1, in which the conditioned medium has a serum-free constituent with a total protein content above 10 µg/ml.

12. The method of claim 11, wherein said serum-free constituent has a total protein content above 100 µg/ml.

13. The method of claim 11, wherein said serum-free constituent has a total protein content above 1 mg/ml.

14. The method of claim 1, in which the conditioned medium is concentrated prior to use.

15. The method of claim 14, wherein said conditioned medium is concentrated by ultrafiltration prior to use.

16. The method of claim 1, further comprising the step of subculturing the hair inductive cells in the culture medium for three or more passages.

17. The method of claim 16, wherein said hair inductive cells are subcultured for seven or more passages.

18. The method of claim 1, further comprising the step of harvesting or isolating cultured or subcultured hair inductive cells.

19. The method of claim 1, in which the hair inductive cells are allogeneic to the prostate epithelial cells.

20. The method of claim 1, in which the hair inductive cells are autologous to the prostate epithelial cells.

* * * * *